(12) United States Patent
Ogura (10) Patent No.: US 6,355,000 B1
(45) Date of Patent: Mar. 12, 2002

(54) SUPERIOR-AND-INFERIOR-LIMB BLOOD-PRESSURE INDEX MEASURING APPARATUS

(75) Inventor: Toshihiko Ogura, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/556,417

(22) Filed: Apr. 24, 2000

(30) Foreign Application Priority Data

May 6, 1999 (JP) ............................................ 11-125886

(51) Int. Cl.⁷ ................................................ A61B 5/02
(52) U.S. Cl. ........................ 600/490; 600/492; 600/494
(58) Field of Search .............................. 600/490, 485, 600/481, 492, 493, 494, 495, 496, 497, 498, 499, 500, 503

(56) References Cited

U.S. PATENT DOCUMENTS

| | | | |
|---|---|---|---|
| 5,101,828 A | * 4/1992 | Welkowitz et al. | 600/481 |
| 5,261,414 A | 11/1993 | Aung et al. | |
| 5,265,011 A | * 11/1993 | O'Rourke | 600/485 |
| 5,715,826 A | * 2/1998 | Horrocks et al. | 600/485 |
| 5,743,857 A | * 4/1998 | Shinoda et al. | 600/496 |
| 5,791,348 A | 8/1998 | Aung et al. | |
| 5,836,888 A | 11/1998 | Ogura et al. | |

FOREIGN PATENT DOCUMENTS

| | | |
|---|---|---|
| GB | 2 281 782 A | 3/1995 |
| JP | 03162827 | 7/1991 |
| JP | 10286241 | 10/1998 |
| NL | 1003125 | 6/1997 |

* cited by examiner

Primary Examiner—Eric F. Winakur
(74) Attorney, Agent, or Firm—Oliff & Berridge, PLC (57) ABSTRACT

An apparatus for measuring a superior-and-inferior-limb blood-pressure index of a living subject, including a first blood-pressure measuring device which measures a first blood pressure of an inferior limb of the subject, a second blood-pressure measuring device which measures a second blood pressure of a superior limb of the subject, an index determining device for determining the superior-and-inferior-limb blood-pressure index, based on the first blood pressure measured by the first blood-pressure measuring device and the second blood pressure measured by the second blood-pressure measuring device, an information obtaining device which obtains propagation-velocity-relating information relating to a velocity of propagation of a pulse wave which propagates between two different portions of the subject, and a display device which simultaneously displays the superior-and-inferior-limb blood-pressure index determined by the index determining device and the propagation-velocity-relating information obtained by the information obtaining device.

7 Claims, 6 Drawing Sheets

● ··· CURRENT MEASURED VALUES

▲ ··· LAST MEASURED VALUES

■ ··· SECOND LAST MEASURED VALUES

SUPERIOR-AND-INFERIOR-LIMB BLOOD-PRESSURE INDEX MEASURING APPARATUS

BACKGROUND OF THE INVENTION

1. Field of the Invention

The present invention relates to an apparatus for measuring a superior-and-inferior-limb blood-pressure index of a living subject (e.g., a ratio of an inferior-limb blood pressure to a superior-limb blood pressure, or a ratio of a superior-limb blood pressure to an inferior-limb blood pressure), and particularly to the art of evaluating the measured superior-and-inferior-limb blood-pressure index.

2. Related Art Statement

Arteriosclerotic cardiovascular disease is one of major death causes of aged women, e.g., not younger than sixty five years, but there is no general method of finding latent arteriosclerosis. However, it is known that since measuring superior-and-inferior-limb blood-pressure index can be used as a simple and repeatable method to find inferior-limb arterial disease and can be used to check quickly and easily the condition of whole cardiovascular system, the index is useful to identify individuals who need special treatments to reduce its death rate or its incidence rate.

Generally, the above superior-and-inferior-limb blood-pressure index (hereinafter, abbreviated to the "SIL BP index") is obtained or calculated as the ratio of a systolic blood pressure ("BP") of an ankle as the inferior-limb BP to a systolic blood pressure of an upper arm as the superior-limb BP, that is, ankle/arm BP index (abbreviated to "AAI", "API", or "ABI"). If the measured ankle/arm blood pressure index of a living person is smaller than a threshold, e.g., about 0.9, abnormality may be diagnosed on the person.

As explained above, the SIL BP index, represented by the ankle/arm BP index, is used to find the inferior-limb arterial disease. However, even if a living person suffers the disease, the SIL BP index measured from the person may indicate a normal value. For example, in the case where a person has stenosis on a distal side of an abdominal artery but suffers arteriosclerosis in not only inferior limbs but also whole body, the SIL BP index measured from the person will indicate a normal value.

SUMMARY OF THE INVENTION

It is therefore an object of the present invention to provide a superior-and-inferior-limb blood-pressure ("SIL BP") index measuring apparatus which assures that, in the case where the SIL BP index measured from a person indicates a normal value, a medical staff such as a doctor or a nurse can judge whether the normal SIL BP index value has resulted from the arteriosclerosis of the whole body of the person.

The Inventor has made various studies and found that, in the case where the SIL BP index is measured together with pulse-wave-propagation-velocity relating information which is known as an index which can be used to evaluate the degree of arteriosclerosis of the whole body of a person, a medical staff can judge whether a normal SIL BP index value measured from the person has resulted from the arteriosclerosis of the whole body of the person. The present invention has been developed based on this finding. As far as the present invention is concerned, the term "pulse-wave-propagation-velocity relating information" is defined as including pulse-wave-propagation-velocity information which is obtained as pulse-wave propagation velocity itself or pulse-wave propagation time, and corrected pulse-wave-propagation-velocity information which is obtained by correcting the pulse-wave-propagation-velocity information to correspond to a reference BP value.

(1) According to a first feature of the present invention, there is provided an apparatus for measuring a superior-and-inferior-limb blood-pressure index of a living subject, comprising a first blood-pressure measuring device which measures a first blood pressure of an inferior limb of the subject; a second blood-pressure measuring device which measures a second blood pressure of a superior limb of the subject; index determining means for determining the superior-and-inferior-limb blood-pressure index, based on the first blood pressure measured by the first blood-pressure measuring device and the second blood pressure measured by the second blood-pressure measuring device; an information obtaining device which obtains propagation-velocity-relating information relating to a velocity of propagation of a pulse wave which propagates between two different portions of the subject; and a display device which simultaneously displays the superior-and-inferior-limb blood-pressure index determined by the index determining means and the propagation-velocity-relating information obtained by the information obtaining device. The phrase "simultaneously displays the SIL BP index and the propagation-velocity-relating ("PVR") information means that a time duration of displaying of the SIL BP index at least partly overlaps a time duration of displaying of the PVR information.

According to this feature, the index determining means determines an SIL BP index value based on the first BP value measured by the first BP measuring device and the second BP value measured by the second BP measuring device, and the information obtaining device obtains PVR information relating to the velocity of propagation of pulse wave which propagates between two different portions of the subject. In addition, the display device simultaneously displays the SIL index value determined by the index determining means and the PVR information obtained by the information obtaining device. Therefore, even if the thus determined SIL index value is normal, a medical staff can judge that the normal SIL index value has resulted from the arteriosclerosis of the whole body of the person, if the obtained PVR information is abnormal.

(2) According to a second feature of the present invention that includes the first feature (1), the apparatus further comprises an identifying device which identifies each one of a plurality of living subjects from the other living subjects; and a storing device which stores, for the each one living subject identified by the identifying device, at least one first superior-and-inferior-limb blood-pressure index value determined by the index determining means and at least one first propagation-velocity-relating information obtained by the information obtaining device, and the display device displays, for the each one living subject, the first superior-and-inferior-limb blood-pressure index value and the first propagation-velocity-relating information which are stored in the storing device, and a second superior-and-inferior-limb blood-pressure index value currently determined by the index determining means and a second propagation-velocity-relating information currently obtained by the information obtaining device, so that an observer can compare the first and second superior-and-inferior-limb blood-pressure index values with each other and compare the first and second propagation-velocity-relating information with each other. According to this feature, the display device displays, for each one living subject, the first SIL BP index value and PVR information stored in the storing device, and the second SIL BP index value currently determined by the index determining means and a second PVR information currently obtained by the information obtaining device, so that an observer can compare the first and second SIL BP index values with each other and compare the first and second PVR information with each other. Thus, the medical staff can easily recognize the respective degrees of advancement of the inferior-limb arteriostenosis and the general arteriosclerosis.

(3) According to a third feature of the present invention that includes the first or second feature (1) or (2), the display device comprises simultaneously displaying means for displaying, in a two-dimensional plane which is defined by a first axis representing superior-and-inferior-limb blood-pressure index and a second axis representing propagation-velocity-relating information, a symbol at a position corresponding to the superior-and-inferior-limb blood-pressure index determined by the index determining means and the propagation-velocity-relating information obtained by the information obtaining device. According to this feature, the medical staff can evaluate, in one glance, the determined SIL BP index value and the obtained PVR information.

(4) According to a fourth feature of the present invention that includes the second or third feature (2) or (3), the display device comprises timewise-change displaying means for displaying, in a two-dimensional plane which is defined by a first axis representing superior-and-inferior-limb blood-pressure index and a second axis representing propagation-velocity-relating information, at least one first symbol at at least one position corresponding to the at least one first superior-and-inferior-limb blood-pressure index value and the at least one first propagation-velocity-relating information which are stored in the storing device, and a second symbol at a position corresponding to the second superior-and-inferior-limb blood-pressure index value currently determined by the index determining means and the second propagation-velocity-relating information currently obtained by the information obtaining device. According to this feature, the medical staff can easily recognize, in one glance, the respective degrees of advancement of the inferior-limb arteriostenosis and the general arteriosclerosis.

(5) According to a fifth feature of the present invention that includes any one of the first to fourth features (1) to (4), the index determining means comprises means for determining, as the superior-and-inferior-limb blood-pressure index, a ratio of the first blood pressure to the second blood pressure, or a ratio of the second blood pressure to the first blood pressure.

(6) According to a sixth feature of the present invention that includes any one of the first to fifth features (1) to (5), the information obtaining device comprises two pulse-wave sensors which are worn on the two different portions of the living subject, respectively, and each of which detects the pulse wave at a corresponding one of the two portions.

(7) According to a seventh feature of the present invention that includes any one of the second to sixth features (2) to (6), the identifying device comprises an input device which is operable by an operator for inputting a batch of identification information identifying the each one living subject from the other living subjects; a memory device which stores a plurality of batches of identification information identifying the plurality of living subjects, respectively; and judging means for judging the batch of identification information input through the input device is identical with each of batches of identification information stored in the memory device, and thereby identifying the each one living subject from the other living subjects.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
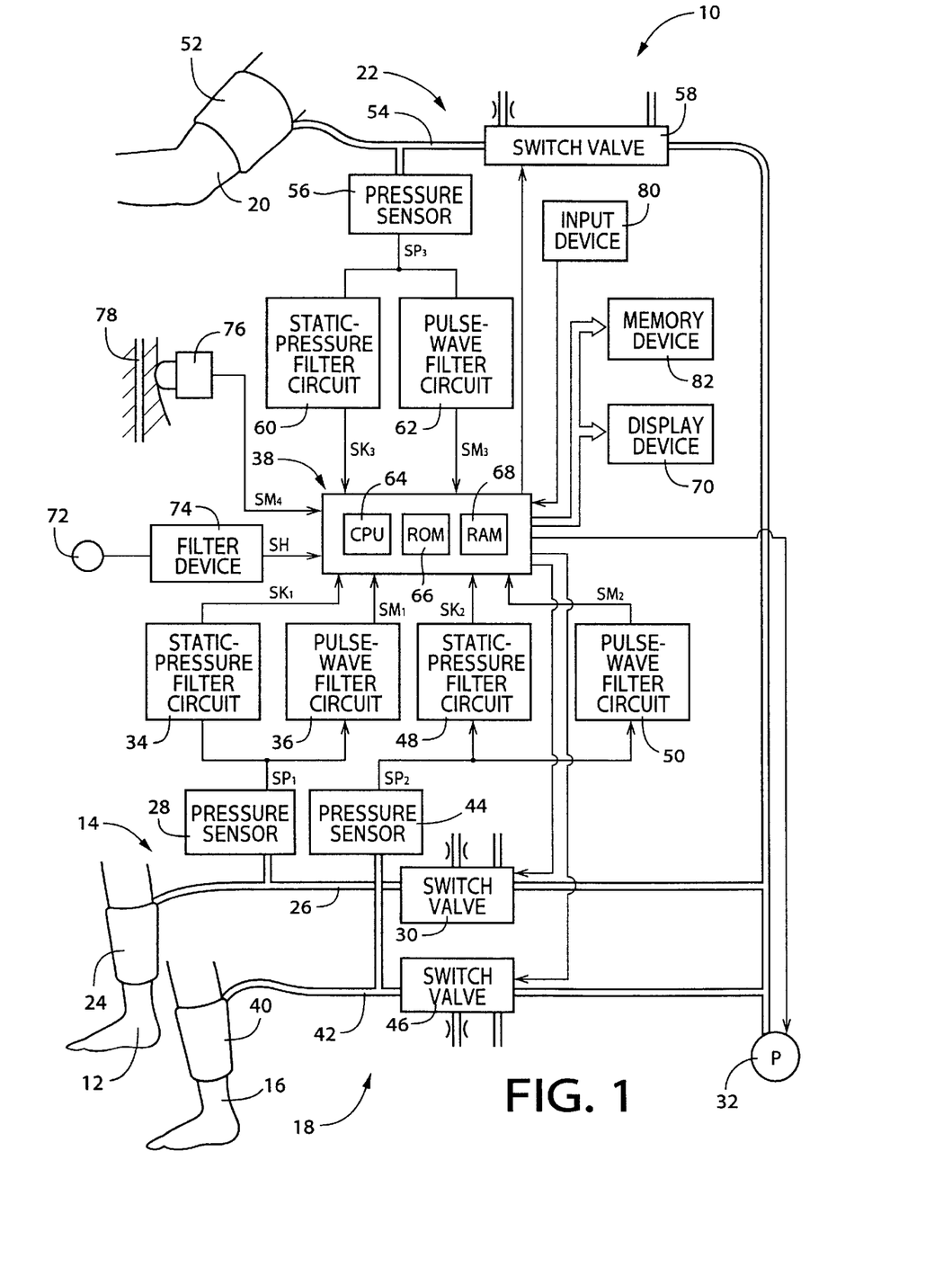
FIG. 1 is a diagrammatic view of the construction of an ankle/arm blood-pressure ("BP") index measuring apparatus to which the present invention is applied.

Hereinafter, there will be described an ankle/arm blood-pressure ("BP") index measuring apparatus 10 to which the present invention is applied, by reference to the drawings. FIG. 1 is a block diagram showing the construction of the measuring apparatus 10. The ankle/arm BP index measuring apparatus 10 is a sort of superior-and-inferior-limb BP index measuring apparatus, since the measuring apparatus 10 measures, as an inferior-limb BP value, a BP value from an ankle of a patient as a living person and measures, as a superior-limb BP value, a BP value from an upper arm of the patient. The present apparatus 10 carries out the BP measurements on the patient who takes the face-down, lateral, or face-up position so that the upper arm and the ankle are substantially level with each other.

In FIG. 1, the ankle/arm BP index measuring apparatus 10 includes a right-leg first BP measuring device 14 which measures a BP value from a right ankle 12 of the patient, a left-leg first BP measuring device 18 which measures a BP value from a left ankle 16 of the patient, and a second BP measuring device 22 which measures a BP value from an upper arm 20 of the patient.

The right-leg first BP measuring device 14 includes an inflatable cuff 24 which includes a belt-like cloth bag and a rubber bag accommodated in the cloth bag and which is wound around the right ankle 12 of the patient; a piping 26; and a pressure sensor 28, a switch valve 30, and an air pump 32 which are connected to the cuff 24 via the piping 26. The switch valve 30 is selectively placed in one of three operation states, that is, (a) a pressurized-air-supply state in which the switch valve 30 allows pressurized air to be supplied from the air pump 32 to the cuff 24, (b) a slow-deflation state in which the valve 30 allows the pressurized air to be deflated slowly at an arbitrary rate from the cuff 24, and (c) a quick-deflation state in which the valve 30 allows the pressurized air to be deflated quickly from the cuff 24.

The pressure sensor 28 detects an air pressure in the cuff 24, and supplies a pressure signal, $SP_1$, representing the detected air pressure, to a static-pressure filter circuit 34 and a pulse-wave filter circuit 36. The static-pressure filter circuit 34 includes a low-pass filter which allows only low frequencies to pass therethrough and thereby selects, from the pressure signal $SP_1$, a cuff-pressure signal, $SK_1$, representing a cuff pressure, $P_{C1}$, as the constant component of the detected air pressure. The filter circuit 34 supplies the cuff-pressure signal $SK_1$ to an electronic control device 38 via an analog-to-digital ("A/D") converter (not shown).

The pulse-wave filter circuit 36 includes a bandpass filter which allows only specific frequencies to pass therethrough and thereby selects, from the pressure signal $SP_1$, a pulse-wave signal, $SM_1$, representing a pulse wave as the oscillatory component of the detected air pressure. The filter circuit 36 supplies the pulse-wave signal $SM_1$ to the electronic control device 38 via an A/D converter (not shown).

The left-leg first BP measuring device 18 includes an inflatable cuff 40, a piping 42, a pressure sensor 44, and a switch valve 46 which have respective constructions identical with those of the counterparts 24, 26, 28, 30 of the right-leg first BP measuring device 14. The switch valve 46 is connected to the air pump 32. The pressure sensor 44 detects an air pressure in the cuff 40, and supplies a pressure signal, $SP_2$, representing the detected air pressure, to a static-pressure filter circuit 48 and a pulse-wave filter circuit 50 which have respective constructions identical with those of the counterparts 34, 36 of the right-leg first BP measuring device 14. The static-pressure filter circuit 48 selects, from the pressure signal $SP_2$, a cuff-pressure signal, $SK_2$, representing a cuff pressure, $P_{C2}$, as the constant component of the detected air pressure, and supplies the cuff-pressure signal $SK_2$ to the control device 38 via an A/D converter (not shown). The pulse-wave filter circuit 50 selects, from the pressure signal $SP_2$, a pulse-wave signal, $SM_2$, representing a pulse wave as the oscillatory component of the detected air pressure, and supplies the pulse-wave signal $SM_2$ to the control device 38 via an A/D converter (not shown).

The second BP measuring device 22 includes an inflatable cuff 52 which has a construction identical with the cuff 24 or 40 and which is wound around an upper arm 20 (e.g., a right upper arm) of the patient; and a piping 54, a pressure sensor 56, and a switch valve 58 which have respective constructions identical with those of the counterparts 24, 26, 28, 30 of the right-leg first BP measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the counterparts 34, 36 of the right-leg first BP measuring device 14. The static-pressure filter circuit 60 selects, from the pressure signal $SP_3$, a cuff-pressure signal, $SK_3$, representing a cuff pressure, $P_{C3}$, as the constant component of the detected air pressure, and supplies the cuff-pressure signal $SK_3$ to the control device 38 via an A/D converter (not shown). The pulse-wave filter circuit 62 selects, from the pressure signal $SP_3$, a pulse-wave signal, $SM_3$, representing a pulse wave as the oscillatory component of the detected air pressure, and supplies the pulse-wave signal $SM_3$ to the control device 38 via an A/D converter (not shown).

The electronic control device 38 is essentially provided by a microcomputer including a central processing unit ("CPU") 64, a read only memory ("ROM") 66, a random access memory ("RAM") 68, and an input-and-output ("I/O") port (not shown), and processes input signals according to control programs pre-stored in the ROM 66, while utilizing the temporary-storage function of the RAM 68. The control device 38 outputs, from the I/O port, drive signals to the air pump 32 and the three switch valves 30, 46, 58 to control the respective operations thereof, and display signals to a display device 70 to control the contents displayed thereby.

A microphone 72 is attached, with an adhesite tape (not shown), to the skin of central portion of the chest of the patient, more specifically described, a prescribed heart-sound-detect position right above the apex cordis, the left end of the fourth intercostal sternum, the left end of the second intercostal sternum, the right end of the second intercostal sternum, or the right end of the fourth intercostal sternum. The microphone 72 detects heart sounds which are transmitted from the heart to the skin of the prescribed heart-sound-detect position. The heart sounds includes a first or I sound which is produced when the heart starts outputting blood to the aorta, and a second or II sound which is produced when the heart ends outputting blood to the aorta. Thus, the heart sounds provide a pulse wave which is produced from the most upstream portion of the aorta. Therefore, the microphone 72 functions as a first pulse-wave detecting device.

Figure 2:
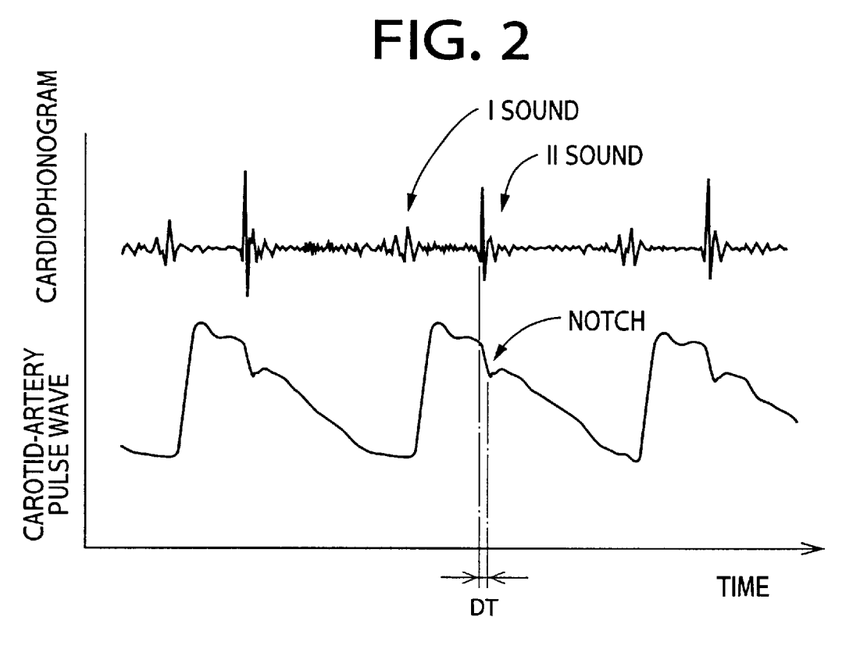
FIG. 2 is a view for explaining respective examples of a phonocardiogram detected by a microphone of the measuring apparatus of FIG. 1 and a carotid-artery pulse wave detected by a carotid-artery pulse-wave sensor of the same apparatus.

The microphone 72 includes a piezoelectric element (not shown) which converts the sounds detected thereby into an electric signal, i.e., a heart-sound signal, SH, and outputs the heart-sound signal SH, which subsequently is amplified by a preamplifier (not shown) and is supplied to a filter device 74. Then, the signal SH is supplied to the control device 38 via a main amplifier and an A/D converter (both not shown). The filter device 74 includes four sorts of filters (not shown) which can be so selected and used that the low-pitched-sound components of the heart-sound signal SH are attenuated and the high-pitched-sound components thereof are exaggerated and accordingly the heart sounds can be heard by the auditory sense of a human being. An upper half portion of FIG. 2 shows an example of a cardiophonogram detected by the microphone 72. The cardiophonogram includes a first or I sound corresponding to the closing of the mitral valve and the opening of the aortic valve and a second or II sound corresponding to the closing of the aortic valve.

The carotid-artery pulse-wave sensor 76 functions as a second pulse-wave detecting device which is worn on a portion of the patient that is located on a downstream side of the microphone 72 as the first pulse-wave detecting device, as seen in the direction of flowing of blood in the body of the patient, and which detects a pulse wave propagating through an artery running in that portion of the patient. The pulse-wave sensor 76 includes a contact member, and a vibration sensor (not shown) which detects vibration of the contact member. The pulse-wave sensor 76 is attached to the neck of the patient such that the contact member is held in pressed contact with the skin right above a carotid artery 78 and detects a carotid-artery pulse wave produced from the carotid artery 78. The pulse-wave sensor 76 supplies a signal, $SM_4$, representing the detected carotid-artery pulse wave, to the control device 38 via an A/D converter (not shown). A lower half portion of FIG. 2 shows an example of the carotid-artery pulse wave detected by the sensor 76. Since the carotid artery 78 has a considerably great diameter and is directly connected to the aorta, the waveform of the carotid-artery pulse wave is substantially identical with that of aortic pulse wave.

An input device 80 includes a keyboard (not shown) through which an identification ("ID") number identifying each patient is input, and which outputs a signal representing the input ID number, to the control device 38. A memory device 82 is provided by a well-known memory such as a magnetic disk, a magnetic tape, a volatile semiconductor memory, or a non-volatile semiconductor memory, and stores, in predetermined memory areas thereof, an ankle/arm BP index (hereinafter, referred to as the "AAI") and pulse-wave-propagation-velocity ("PWV") relating information which are determined and obtained by the control device 38.

Figure 3:
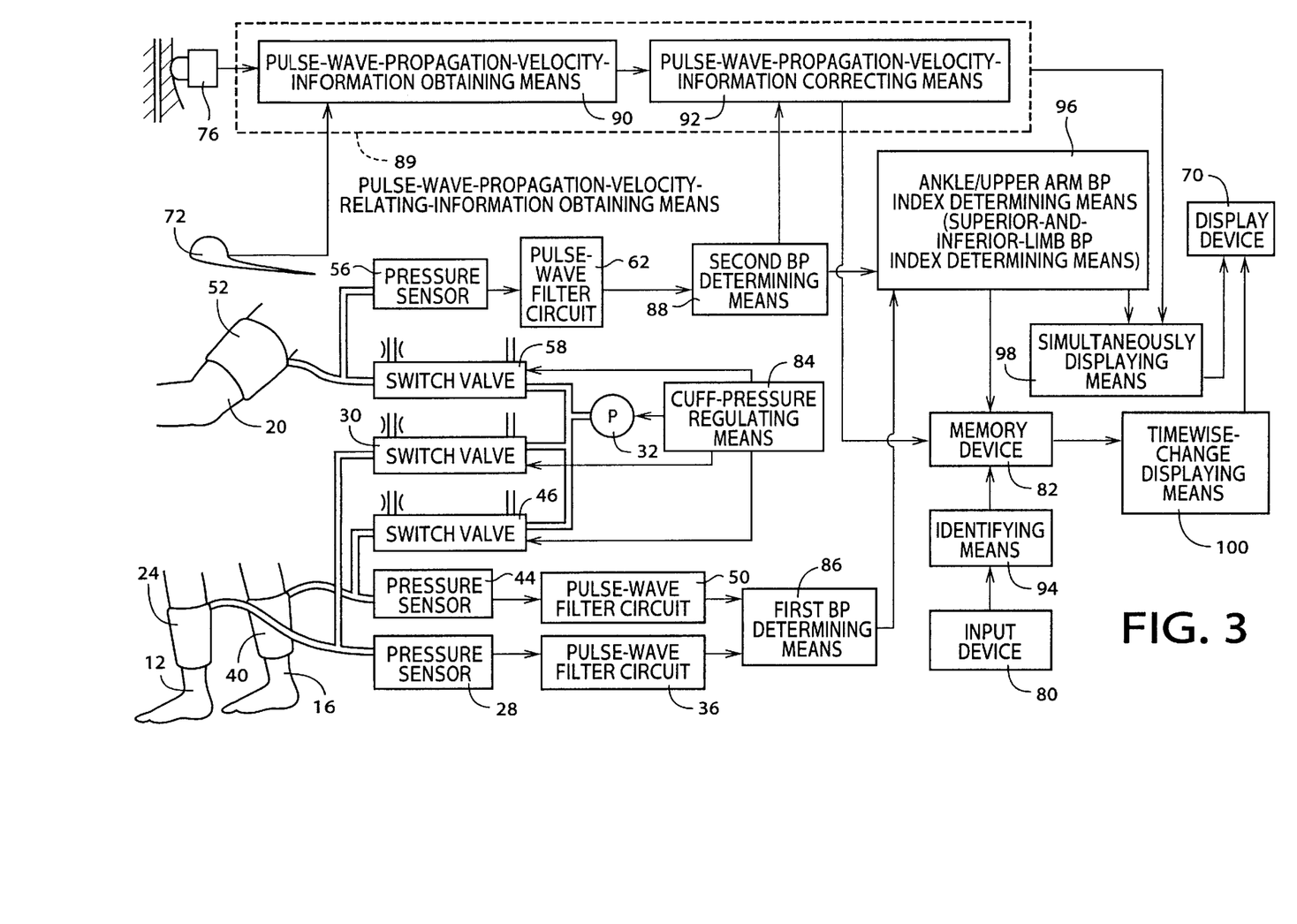
FIG. 3 is a diagrammatic view of important functions of the measuring apparatus of FIG. 1.

FIG. 3 is a diagrammatic view for explaining the important control functions of the control device 38. A cuff-pressure regulating means 84 controls the air pump 32 and the three switch valves 30, 46, 58, such that the respective pressing pressures of the three cuffs 24, 40, 52 are quickly increased up to a predetermined target pressure value, PCM, (e.g., about 180 mmHg) and then are slowly decreased at a rate of about 3 mmHg/sec.

A first BP determining means 86 determines right-leg first BP values, $BP1_R$, that is, BP values of the right ankle 12, according to well-known oscillometric method, based on the change of respective amplitudes of the heartbeat-synchronous pulses of the pulse-wave signal $SM_1$ detected one by one during the slow deflation of the cuff 24 wound around the right ankle 12 under the control of the cuff-pressure regulating means 84. In addition, the first BP determining means 86 determines left-leg first BP values, $BP1_L$, that is, BP values of the left ankle 16, according to the oscillometric method, based on the change of respective amplitudes of the heartbeat-synchronous pulses of the pulse-wave signal $SM_2$ detected one by one during the slow deflation of the cuff 40 wound around the left ankle 16 under the control of the cuff-pressure regulating means 84. The right-leg first BP values $BP1_R$ include a systolic BP value $BP1_{RSYS}$ and a diastolic BP value $BP1_{RDIA}$, and the left-leg first BP values $BP1_L$ include a systolic BP value $BP1_{LSYS}$ and a diastolic BP value $BP1_{LDIA}$. Hereinafter, when it is not needed to distinguish the right-leg first BP values $BP1_R$ and the left-leg first BP values $BP1_L$ from each other, those BP values will be wholly referred to as the first BP values BP1.

A second BP determining means 88 determines second BP values, BP2, (systolic BP value $BP2_{SYS}$ and diastolic BP value $BP2_{DIA}$), that is, BP values of the upper arm 20, according to the well-known oscillometric method, based on the change of respective amplitudes of the heartbeat-synchronous pulses of the pulse-wave signal SM3 detected one by one during the slow deflation of the cuff 52 wound around the upper arm 20 under the control of the cuff-pressure regulating means 84.

A PWV-information obtaining means 90 as part of a PWV-relating-information obtaining means 89 iteratively obtains PWV information based on a time difference between a periodic point on each of the heartbeat-synchronous pulses of the first pulse wave detected by the microphone 72 as the first pulse-wave detecting device, and a periodic point on a corresponding one of the heartbeat-synchronous pulses of the second pulse wave detected by the sensor 76 as the second pulse-wave detecting device. For example, the PWV-information obtaining means 90 includes a time-difference calculating means which calculates a time difference (i.e., pulse-wave propagation time), DT, shown in FIG. 2, that is, a time difference between a time point at which the microphone 72 detects the commencement of second or II heart sound (this point corresponds to a notch of the aortic pulse wave where the amplitude quickly decreases and then starts increasing), and a time point at which the sensor 76 detects the notch of the carotid-artery pulse wave. The PWV-information obtaining means 90 iteratively calculates, based on the time difference DT calculated by the time-difference calculating means for each of the heartbeat-synchronous pulses, a velocity PWV (m/sec) at which the pulse wave propagates through the artery of the patient, according to the following expression pre-stored in the ROM 66:

$PWV=L/DT$ where L (m) is the distance from the left ventricle of the heart, via the aorta, to the position where the sensor 76 is worn, and is replaced with a constant value which is experimentally obtained in advance.

A PWV-information correcting means 92 as another part of the PWV-relating-information obtaining means 89 corrects the PWV information calculated by the PWV-information obtaining means 90, so that the corrected PwV information corresponds to a reference BP value, e.g., 80 mmHg. This corrected PWV information is known as an index which can be used to evaluate the degree of general or systemic arteriosclerosis of a living person, and can be obtained in various methods including the following two methods. The first method is to obtain corrected PWV information based on a BP value BP which is determined by a BP determining means, such as the first or second BP determining means 86, 88, with respect to a prescribed portion of a living person; and the second method is to obtain corrected PWV information based on a PWV information and a BP relating information which are actually obtained from a living person, according to a predetermined relationship between (A) (a1) PWV information and (a2) BP relating information and (B) corrected PWV information. Here, the BP relating information is defined as information which changes as the BP of the person changes, and may be an ejection time, ET, during which blood is output from the left ventricle of the heart; a pre-ejection period, PEP, from the commencement of systole of muscle of the left ventricle to the commencement of outputting of blood from the left ventricle; or a heart rate, HR.

Figure 4:
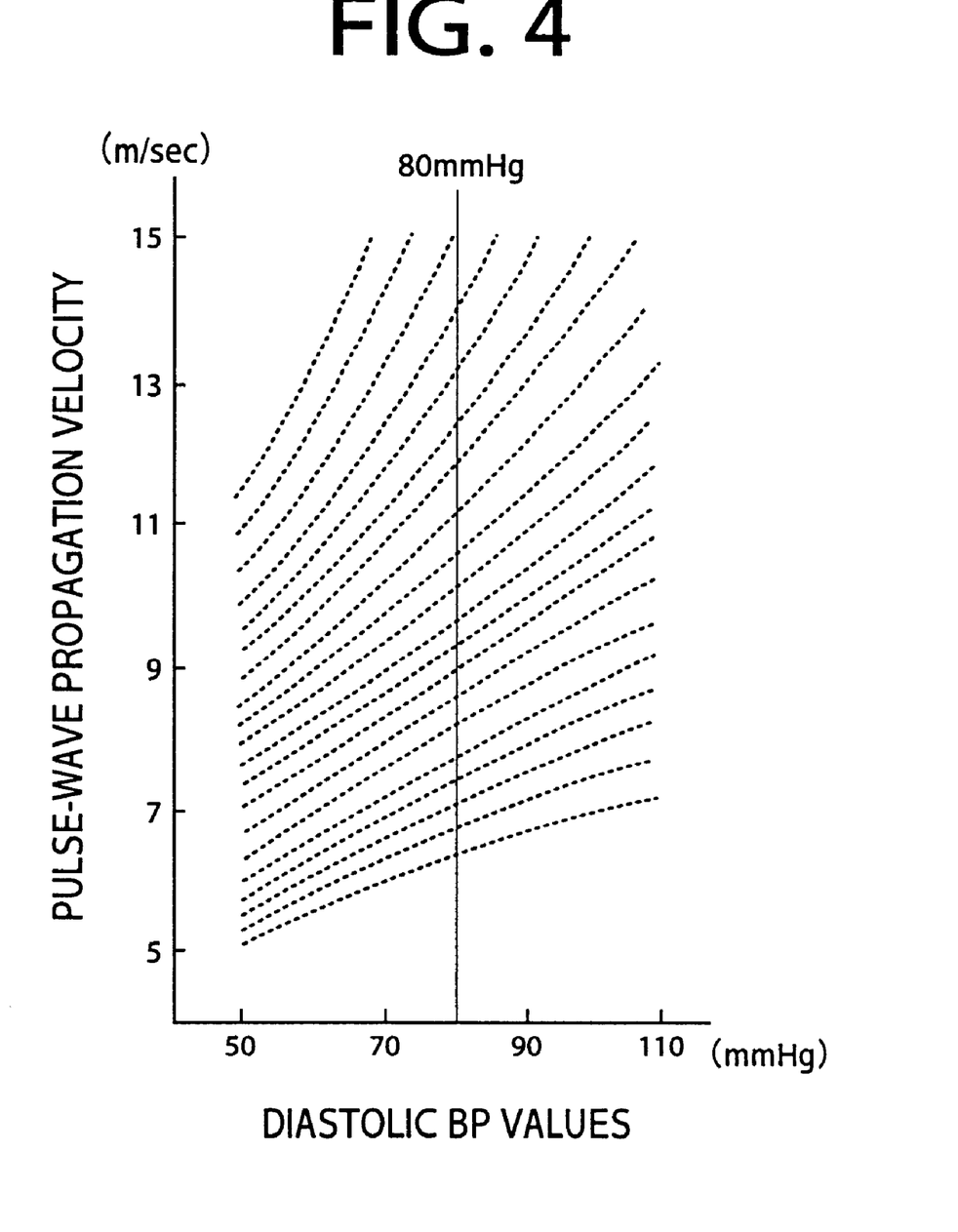
FIG. 4 is a view of a map representing a relationship between diastolic BP values and pulse-wave propagation velocity values, the map being used by the measuring apparatus of FIG. 1.

In the case where the above-indicated first method is employed, the ROM 66 stores a map, shown in FIG. 4, which models or represents a relationship between PWV values and diastolic BP values. The map include a plurality of curves which correspond a plurality of diastolic BP values, respectively. Based on the diastolic BP value and the PWV value which are actually calculated by the first or second BP determining means 86, 88 and the PWV-information obtaining means 90, the control device 38 selects one of the curves that is the most approximate to both the calculated diastolic BP value and PWV value, and determines, as the corrected value, $PWV_C$, a value on the selected curve that corresponds to the reference BP value, i.e., 80 mmHg.

An identifying means 94 identifies the ID number of each patient that is input from the input device 80, and stores, in association with the ID number of each patient, the corrected PWV value $PWV_C$ of each patient, in the memory device 82.

An ankle/arm BP index determining means 96 as the SIL BP index determining means determines or calculates an ankle/arm BP index value ("AAI") based on a first BP value BP1 determined by the first BP determining means 86 and a corresponding second BP value BP2 determined by the second BP determining means 88 (e.g., the systolic first BP value $BP1_{SYS}$ corresponds to the systolic second BP value $BP2_{SYS}$, and the diastolic first BP value $BP1_{DIA}$ corresponds to the diastolic second BP value $BP2^{DIA}$). For example, the AAI may be obtained by dividing the first BP value BP1 by the corresponding second BP value BP2, or dividing the second BP value BP2 by the corresponding second BP value BP1. The thus determined AAI value is stored in association with the ID number in the memory device 82.

A simultaneously displaying means 98 controls the display device 70 to display simultaneously the PWV information obtained by the PWV-relating-information obtaining means 89, and the AAI value calculated by the ankle/arm BP index determining means 96. For example, the displaying means 98 controls the display device 70 to display simultaneously a value representing the PWV information and the AAI value, side by side, on a screen thereof. More specifically described, the displaying means 98 controls the display device 70 to display, in a two-dimensional plane defined by a first axis representing AAI values and a second axis representing PWV values, a symbol or an indicia at a position corresponding to the AAI value actually determined by the determining means 96 and the corrected PWV value $PWV_C$ determined by the PWV-relating-information obtaining means 89.

A time-wise-change displaying means 100 displays, in the above-indicated two-dimensional plane, at least one first symbol at at least one position corresponding to at least one AAI value and at least one corresponding PWV-relating information which have been stored, for each patient, in the respective memory areas of the memory device 82 in at least one past or prior measurement operation, and a second symbol at a position corresponding to an AAI value which is currently determined, for the each patient, by the ankle/arm BP index determining means 96 in the current measurement operation and a PWV-relating information which is currently obtained for the each patient by the PWV-relating-information obtaining means 89 in the current measurement operation. The first and second symbols or indicias may be identical with each other. However, it is preferred that the first and second symbols be different from each other so that an observer can easily distinguish the two symbols from each other.

Figure 5:
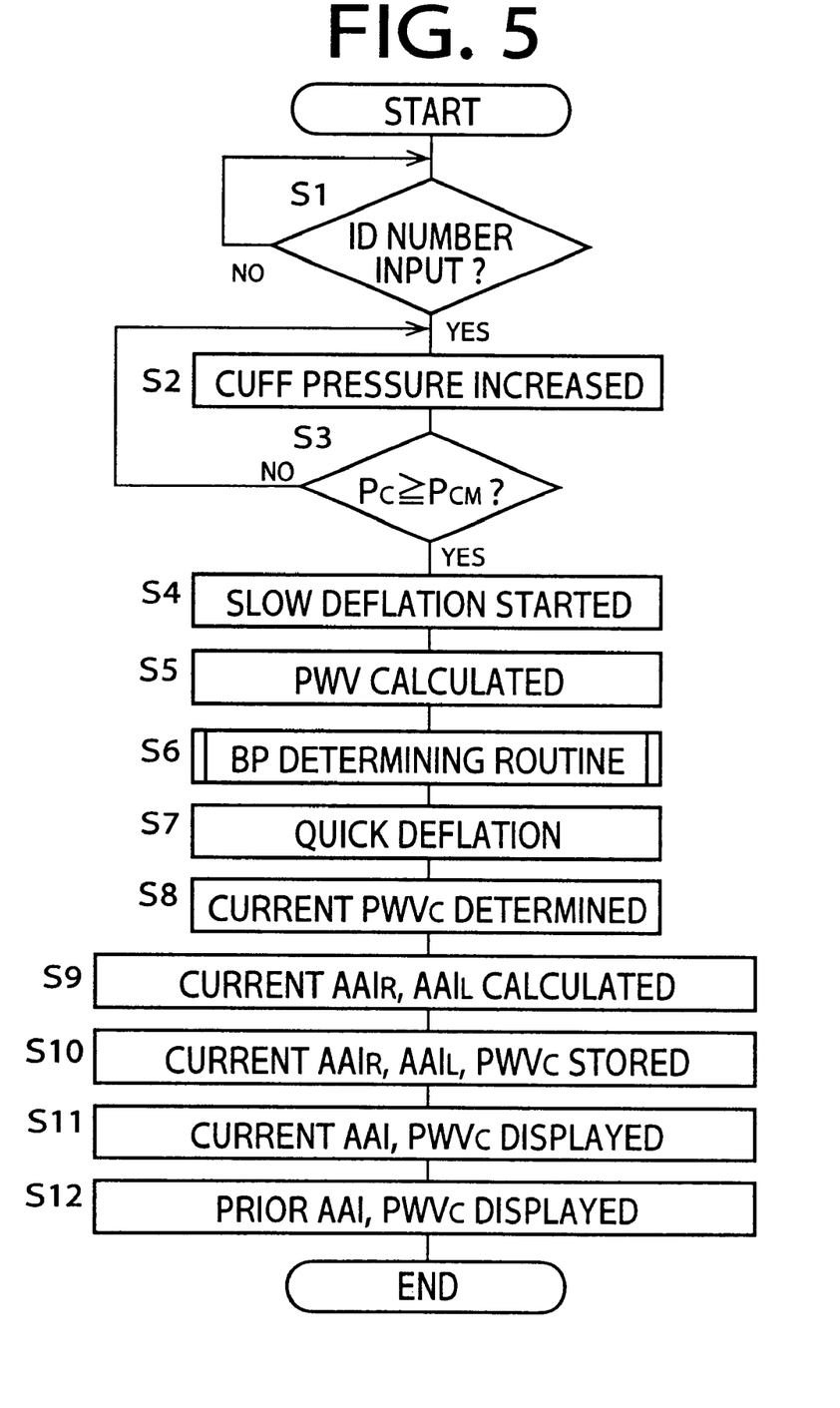
FIG. 5 is a flow chart representing a control program according to which an electronic control device of the measuring apparatus of FIG. 1 is operated.

FIG. 5 is a flow chart representing a control program according to which the control device 38 is operated. First, at Step S1 corresponding to the identifying means 94, the control device 38 judges whether an ID number has been input through the input device 80. This step is repeated until a positive judgment is made at Step S1. Meanwhile, when an ID number is input and a positive judgment is made, the control of the control device 38 goes to Steps S2, S3, and S4 corresponding to the cuff-pressure regulating means 84. At Step S2, the three switch valves 30, 46, 58 are switched to their pressure-supply positions and the air pump 32 is operated, so that the respective air pressures of the three cuffs 24, 40, 52 are quickly increased. At Step S3, it is judged whether all the air pressures PC of the three cuffs 24, 40, 52 have reached the predetermined target pressure value PCM (about 180 mmHg). If a negative judgment is made at Step S3, Steps S2 and S3 are repeated to continue increasing the air pressures PC of the cuffs 24, 40, 52.

If a positive judgment is made at Step S3, the control goes to Step S4 to stop the operation of the air pump 32 and switch the three switch valves 30, 46, 58 to their slow-deflation positions, so that the respective air pressures $P_C$ of the three cuffs 24, 40, 52 are decreased slowly at a predetermined low rate of about 3 mmHg/sec.

Step S4 is followed by Step S5 corresponding to the PWV-relating-information obtaining means 90. At Step S5, the control device 38 calculates, as shown in FIG. 2, a time difference between a time when the microphone 72 detects the second or II heart sound and a time when the carotid-artery pulse-wave sensor 76 detects the notch of carotid-artery pulse wave, i.e., a pulse-wave propagation time DT that is a time needed for a pulse wave to propagate from the heart to the position where the sensor 76 is worn. The control device 38 calculates a pulse-wave propagation velocity PWV based on the thus calculated pulse-wave propagation time DT according to the above-indicated expression: PWV=L/DT.

Step S5 is followed by the BP-determine routine of Step S6, corresponding to the first BP determining means 86 and the second BP determining means 88. More specifically described, the control device 38 determines an amplitude of each of successive heartbeat-synchronous pulses of the cuff pulse wave represented by the pulse-wave signal $SM_1$ supplied from the pulse-wave filter circuit 36, and determines a right-leg first systolic BP value $BP1_{RSYS}$ based on the time-wise change of the thus determined amplitudes according to a well-known oscillometric BP-determine algorithm. Similarly, the control device 38 determines an amplitude of each of successive heartbeat-synchronous pulses of the cuff pulse wave represented by the pulse-wave signal $SM_2$ supplied from the pulse-wave filter circuit 50, and determines a left-leg first systolic BP value $BP1_{LSYS}$ based on the time-wise change of the thus determined amplitudes according to the oscillometric BP-determine algorithm. In addition, the control device 38 determines an amplitude of each of successive heartbeat-synchronous pulses of the cuff pulse wave represented by the pulse-wave signal $SM_3$ supplied from the pulse-wave filter circuit 62, and determines second systolic and diastolic BP values $BP2_{SYS}$, $BP2_{DIA}$, based on time-wise change of the thus determined amplitudes according to the oscillometric BP-determine algorithm.

Step S6 is followed by Step S7 corresponding to the cuff-pressure regulating means 84. At Step S7, the three switch valves 30, 46, 58 are switched to their quick-deflation positions, so that the respective air pressures of the three cuffs 24, 40, 52 are quickly decreased.

Step S7 is followed by Step S8 corresponding to the PWV-information correcting means 92. At Step S8, the control device 38 selects one of the plurality of curves, stored in the ROM 66 and shown in FIG. 4, that is the nearest to the point defined by the pulse-wave propagation velocity PWV determined at Step S5 and the second diastolic BP value $BP2_{DIA}$ determined at Step S6. The control device 38 determines, as the corrected pulse-wave propagation velocity $PWV_C$, a value which is indicated by the thus selected curve at 80 mmHg.

Step S8 is followed by Step S9 corresponding to the ankle/arm BP index determining means 96. At Step S9, the control device 38 calculates a right ankle/arm BP index $AAI_R$ by dividing the right-leg first systolic. BP value $BP1_{RSYS}$ determined at Step S6 by the second systolic BP value $BP2_{SYS}$ determined at Step S6, and calculates a left ankle/arm BP index $AAI_L$ by dividing the left-leg first systolic BP value $BP1_{LSYS}$ determined at Step S6 by the second systolic BP value $BP2_{SyS}$.

Step S9 is followed by Step S10 to store, in association with the ID number input at Step S1, the right and left ankle/arm BP index values $AAI_R$, $AAI_L$ determined at Step S9, together with the corrected pulse-wave propagation velocity PWVC determined at Step S8, in an appropriate memory area of the memory device 82.

Figure 6:
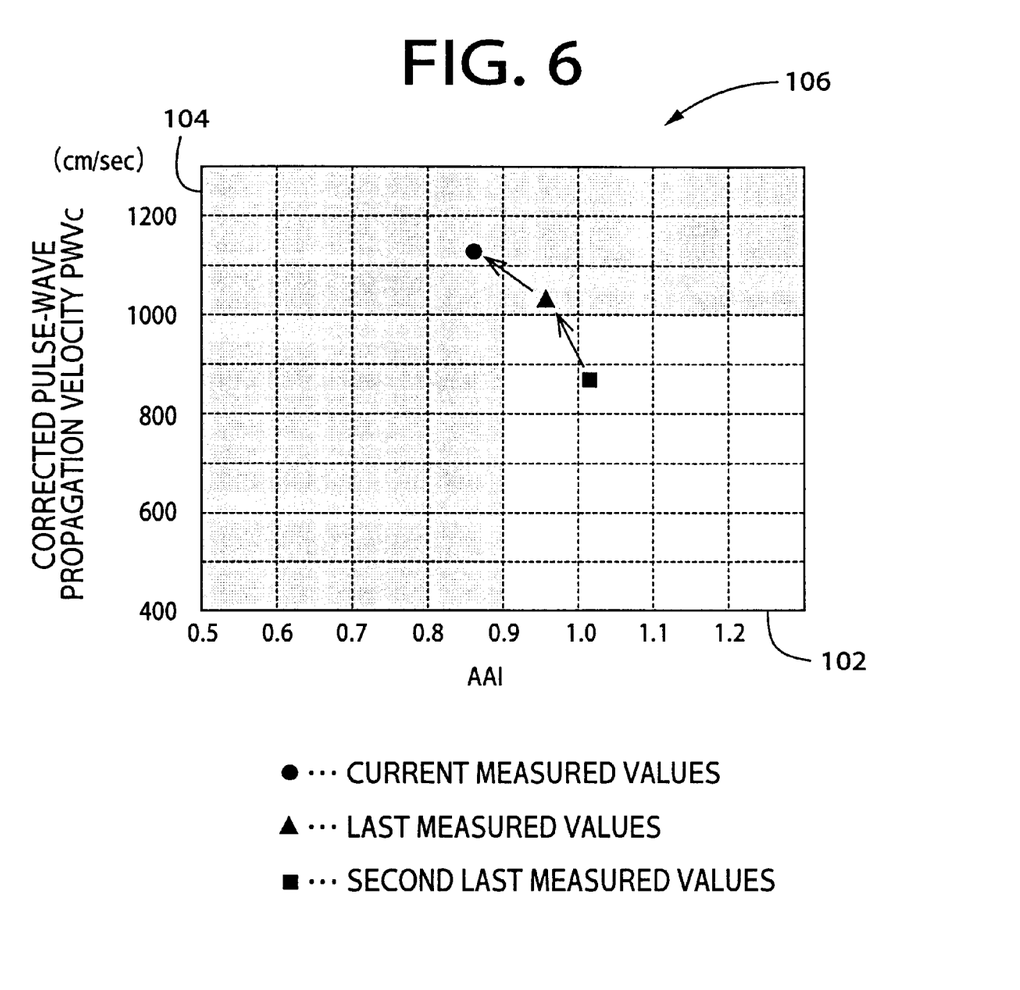
FIG. 6 is a two-dimensional graph which is displayed by a display device of the measuring apparatus of FIG. 1 and which shows the ankle/arm BP index values and the corrected pulse-wave propagation velocity values which are determined by the measuring apparatus of FIG. 1.

Step S10 is followed by Step S11 corresponding to the simultaneously displaying means 98. At Step S11, the control device 38 controls the display device 70 to display, in a two-dimensional graph 106 defined by a first axis 102 representing ankle/arm BP index AAI and a second axis 104 representing corrected pulse-wave propagation velocity $PWV_C$, a symbol ("black circle") at a position defined by the smaller one of the right and left ankle/arm BP index values $AAI_R$, $AAI_L$ determined at Step S9, and the corrected pulse-wave propagation velocity PWVC determined at Step S8. The display device 70 displays, in its screen image, the two-dimensional graph 106, for easier diagnosis purposes, in such a manner that a background color of an abnormal area corresponding to one or both of an abnormal range (not greater than 0.9) of the ankle/arm BP index values AAI and an abnormal range (not smaller than 1,000 cm/sec) of the corrected pulse-wave propagation velocity PWVC differs from that of a normal area corresponding to both of a normal range (greater than 0.9) of the ankle/arm BP index values AAI and a normal range (smaller than 1,000 cm/sec) of the corrected pulse-wave propagation velocity $PWV_C$.

Step S11 is followed by Step S12 corresponding to the timewise-change displaying means 100. At Step S12, the control device 38 displays, in the two-dimensional graph 106, at least one symbol at at least one position defined by the smaller one of the right and left ankle/arm BP index values $AAI_R$, $AAI_L$ that had determined in at least one past measuring operation and have been stored, in association with the ID number input at Step S1, in the memory device 82, and the corrected pulse-wave propagation velocity PWVC determined in the same measuring operation and stored in association with the ID number in the same device 82. FIG. 6 shows an example in which the current measuring operation for the patient having the ID number input at Step S1 is the third measuring operation. FIG. 6 shows, in addition to the different symbol ("black circle") corresponding to the current or third measuring operation, a symbol ("black triangle") corresponding to the last or second measuring operation, and a different symbol ("black square") corresponding to the second last or first measuring operation. Each pair of successive symbols corresponding to each pair of successive measuring operations are connected to each other by an arrow to indicate the tendency of change of the corresponding two ankle/arm BP index values AAI and the corresponding two pulse-wave propagation velocity values $PWV_C$.

As is apparent from the foregoing description, in the present embodiment, the ankle/arm BP index determining means 96 (S9) determines the ankle/arm BP index AAI by dividing the first systolic BP value $BP1_{SYS}$ determined by the first BP determined means 86 (S6), by the second systolic BP value $BP2_{SYS}$ determined by the second BP determined means 88 (S6), and the PWV-information correcting means 92 provides the corrected pulse-wave propagation velocity $PWV_C$ relating to the pulse-wave propagation velocity PWV at which the pulse wave propagates from the heart to the neck. The simultaneously displaying means 98 (S11) simultaneously displays, in the two-dimensional graph 106 of the display device 70, the ankle/arm BP index AAI and the corrected pulse-wave propagation velocity $PWV_C$. Thus, an observer can judge that, in the case where the ankle/arm BP index AAI is normal but the corrected pulse-wave propagation velocity $PWV_C$ is abnormal, the ankle/arm BP index AAI is normal because the patient suffers arteriosclerosis all over his or her whole body.

In addition, in the present embodiment, the timewise-change displaying means 100 (S12) simultaneously displays, in the two-dimensional graph 106 of the display device 70, not only the ankle/arm BP index AAI and the corrected pulse-wave propagation velocity $PWV_C$ that are currently determined for the patient having the ID number input at Step S1, but also the ankle/arm BP index AAI and the corrected pulse-wave propagation velocity $PWV_C$ that had been determined for the same patient and have been stored in the memory device 82. Thus, the observer can easily read the respective degrees of advancement of the inferior-limb arteriostenosis and the general arteriosclerosis.

Moreover, in the present embodiment, the simultaneously displaying means 98 (S11) displays, in the two-dimensional graph 106 defined by the first axis 102 representing ankle/arm BP index AAI and the second axis 104 representing corrected pulse-wave propagation velocity $PWV_C$, a symbol at a position defined by the ankle/arm BP index value AAI determined by the ankle/arm BP index determining means 92 (S9) and the corrected pulse-wave propagation velocity $PWC_C$ determined by the PWV-information correcting means 92 (S8). Therefore, the observer can evaluate, in one glance, both the ankle/arm BP index AAI and the corrected pulse-wave propagation velocity $PWV_C$.

In addition, in the present embodiment, the timewise-change displaying means 100 (S12) displays, in the two-dimensional graph 106 defined by the first axis 102 representing ankle/arm BP index AAI and the second axis 104 representing corrected pulse-wave propagation velocity $PWV_C$, a symbol at a position defined by the ankle/arm BP index AAI and the corrected pulse-wave propagation velocity $PWV_C$ that are currently determined for the patient having the ID number input at Step S1, and a symbol at a position defined by the ankle/arm BP index AAI and the corrected pulse-wave propagation velocity $PWV_C$ that had been determined for the same patient and have been stored in the memory device 82. Thus, the observer can evaluate, in one glance, the respective degrees of advancement of the inferior-limb arteriostenosis and the general arteriosclerosis.

While the present invention has been described in its preferred embodiment, it may be otherwise embodied.

For example, the two-dimensional graph employed at Steps S11 and S12 of the flow chart of FIG. 5 is defined by the second axis 104 representing corrected pulse-wave propagation velocity $PWV_C$. However, the second axis 104 may be one which represents the pulse-wave propagation velocity PWV, the pulse-wave propagation time DT, or a corrected pulse-wave propagation time $DT_C$ which is obtained by correcting the pulse-wave propagation time DT in the same manner as that in which the corrected pulse-wave propagation velocity $PWV_C$ is obtained by correcting the pulse-wave propagation velocity PWV.

In the illustrated embodiment, each of the right-leg first BP measuring device 14, the left-leg first BP measuring device 16, and the second BP measuring device 22 measures a BP value according to the oscillometric method. However, each of the three BP measuring devices 14, 16, 22 may be one which measures a BP value according to a well-known Korotkoff-sound method in which a BP value is measured based on a cuff-pressure value read at a time when Korotkoff sounds are first or last detected. Otherwise, each device 14, 16, 22 may be one which measures a BP value according to a supersonic Doppler method in which, while a pressure which presses an artery is changed, a supersound emitter and a supersound receiver which are provided right above the artery cooperate with each other to detect the opening and closing of the artery.

At Step S11 of the flow chart of FIG. 5, corresponding to the simultaneously displaying means 98, a symbol is indicated at a position defined by the smaller one selected from the right and left ankle/arm BP index values $AAI_R$, $AAI_L$ determined at Step S9, and the corrected pulse-wave propagation velocity $PWV_C$ determined at Step S8. However, two symbols may be indicated at a first position defined by the right ankle/arm BP index value $AAI_R$ and the corrected velocity $PWV_C$, and at a second position defined by the left ankle/arm BP index value $AAI_L$ and the corrected velocity $PWV_C$, respectively. Similarly, at Step S12 corresponding to the timewise-change displaying means 100, two symbols may be indicated at a first position defined by the right ankle/arm BP index value $AAI_R$ and the corrected velocity $PWV_C$ that had been determined in the past measuring operation, and at a second position defined by the left ankle/arm BP index value $AAI_L$ and the corrected velocity $PWV_C$ that had been determined in the same measuring operation.

In the two-dimensional graph 106 employed in Steps S11 and S12 of the flow chart of FIG. 5, the black-circle, black-triangle, and black-square symbols are used. However, other symbols having different shapes may be used. In addition, three symbols may have different colors so that they can be distinguished from one another. Moreover, three identical symbols may be given suffixed sequential numbers so that they can be distinguished from one another.

Although in the illustrated embodiment the rightleg first BP value $BP1_R$ and the left-leg first BP value $BP1_L$ are measured from the right and left ankles 12, 16 of the patient, respectively, it is possible to measure only one of the two first BP values $BP1_R$, $BP1_L$.

In the illustrated embodiment, the microphone 72 adapted to be worn on the chest of the living person is used as the first pulse-wave sensor to obtain PWV information. However, the first pulse-wave sensor may be provided by an electrocardiograph (ECG) which includes a plurality of electrodes adapted to be adhered to predetermined positions on a living person and continuously detects a pulse wave representing the active potential of the cardiac muscle via the electrodes. In addition, the cuff 52 adapted to be wound around the upper arm 20 and the pressure sensor 56 connected to the cuff 52 may be utilized as the first pulse-wave sensor, and either the cuff 24 adapted to be wound around the right ankle 12 and the pressure sensor 28 connected to the cuff 24 or the cuff 40 adapted to be wound around the left ankle 16 and the pressure sensor 44 connected to the cuff 40 may be utilized as the second pulse-wave sensor. In the last case, the air pressure of each cuff 52, 24 (or 40) is held, before or after each BP measuring operation, at a pre-set value sufficiently lower than a diastolic BP value $BP_{DIA}$ of a living person, and PWV information is obtained based on the pulse wave which is detected by the each cuff being in this state.

In the illustrated embodiment, the input device 80 is operated to input the ID number of the patient, and the identifying means 94 identifies the patient based on the ID number input through the input device 80. However, the ankle/arm BP index measuring apparatus 10 may employ a card reading device which reads an ID card which bears an ID code identifying a patient from other patients, and identifying means for identifying the patient based on the ID code read by the card reading device. Otherwise, the apparatus 10 may employ identifying means for identifying each one patient from other patients, based on information proper to that patient, such as his or her fingerprint or voiceprint.

The ankle/arm BP index measuring apparatus 10 is a sort of inferior-and-superior-limb BP index measuring apparatus wherein an ankle is selected as an inferior limb and an upper arm is selected as a superior limb. However, a femoral portion or a toe may be selected as an inferior limb, and a wrist or a finger may be selected as a superior limb.

It is to be understood that the present invention may be embodied with other changes, improvements, and modifications that may occur to a person skilled in the art without departing from the scope and spirit of the invention defined in the appended claims.

What is claimed is:

1. An apparatus for measuring a superior-and-inferior-limb blood-pressure index of a living subject, comprising:
   a first blood-pressure measuring device which measures a first blood pressure of an inferior limb of the subject;
   a second blood-pressure measuring device which measures a second blood pressure of a superior limb of the subject;
   index determining means for determining the superior-and-inferior-limb blood-pressure index, based on the first blood pressure measured by the first blood-pressure measuring device and the second blood pressure measured by the second blood-pressure measuring device;
   an information obtaining device which obtains propagation-velocity-relating information relating to a velocity of propagation of a pulse wave which propagates from a heart of the subject to each of two different portions of the subject; and
   a display device which simultaneously displays the superior-and-inferior-limb blood-pressure index determined by the index determining means and the propagation-velocity-relating information obtained by the information obtaining device.

2. An apparatus according to claim 1, further comprising:
   an identifying device which identifies each one of a plurality of living subjects from the other living subjects; and
   a storing device which stores, for said each one living subject identified by the identifying device, at least one first superior-and-inferior-limb blood-pressure index value determined by the index determining means and at least one first propagation-velocity-relating information obtained by the information obtaining device,
   wherein the display device displays, for said each one living subject, the first superior-and-inferior-limb blood-pressure index value and the first propagation-velocity-relating information which are stored in the storing device, and a second superior-and-inferior-limb blood-pressure index value currently determined by the index determining means and a second propagation-velocity-relating information currently obtained by the information obtaining device, so that an observer can compare the first and second superior-and-inferior-limb blood-pressure index values with each other and compare the first and second propagation-velocity-relating information with each other.

3. An apparatus according to claim 1, wherein the display device comprises simultaneously displaying means for displaying, in a two-dimensional plane which is defined by a first axis representing superior-and-inferior-limb blood-pressure index and a second axis representing propagation-velocity-relating information, a symbol at a position corresponding to the superior-and-inferior-limb blood-pressure index determined by the index determining means and the propagation-velocity-relating information obtained by the information obtaining device.

4. An apparatus according to claim 2, wherein the display device comprises timewise-change displaying means for displaying, in a two-dimensional plane which is defined by a first axis representing superior-and-inferior-limb blood-pressure index and a second axis representing propagation-velocity-relating information, at least one first symbol at at least one position corresponding to the at least one first superior-and-inferior-limb blood-pressure index value and the at least one first propagation-velocity-relating information which are stored in the storing device, and a second symbol at a position corresponding to the second superior-and-inferior-limb blood-pressure index value currently determined by the index determining means and the second propagation-velocity-relating information currently obtained by the information obtaining device.

5. An apparatus according to claim 1, wherein the index determining means comprises means for determining, as the superior-and-inferior-limb blood-pressure index, a ratio of the first blood pressure to the second blood pressure, or a ratio of the second blood pressure to the first blood pressure.

6. An apparatus according to claim 1, wherein the information obtaining device comprises two pulse-wave sensors which are worn on the two different portions of the living subject, respectively, and each of which detects the pulse wave at a corresponding one of the two portions.

7. An apparatus according to claim 2, wherein the identifying device comprises:

an input device which is operable by an operator for inputting a batch of identification information identifying said each one living subject from said other living subjects;

a memory device which stores a plurality of batches of identification information identifying said plurality of living subjects, respectively; and judging means for judging the batch of identification information input through the input device is identical with each of batches of identification information stored in the memory device, and thereby identifying said each one living subject from said other living subjects.

* * * * *